(12) United States Patent
Kunita et al.

(10) Patent No.: US 8,413,285 B2
(45) Date of Patent: Apr. 9, 2013

(54) ELECTRONIC TOOTHBRUSH

(75) Inventors: Tomohiro Kunita, Hikone (JP); Suehisa Kishimoto, Hikone (JP)

(73) Assignee: Panasonic Electric Works Co., Ltd., Osaka (JP)

(*) Notice: Subject to any disclaimer, the term of this patent is extended or adjusted under 35 U.S.C. 154(b) by 0 days.

(21) Appl. No.: 12/735,583

(22) PCT Filed: Apr. 15, 2009

(86) PCT No.: PCT/JP2009/057597
§ 371 (c)(1),
(2), (4) Date: Jul. 29, 2010

(87) PCT Pub. No.: WO2009/128477
PCT Pub. Date: Oct. 22, 2009

(65) Prior Publication Data
US 2011/0016648 A1    Jan. 27, 2011

(30) Foreign Application Priority Data

Apr. 15, 2008  (JP) ................... 2008-105988
Apr. 15, 2008  (JP) ................... 2008-105989
Apr. 15, 2008  (JP) ................... 2008-105990

(51) Int. Cl.
*A46B 15/00*  (2006.01)
*A61C 17/00*  (2006.01)
*A61C 17/22*  (2006.01)

(52) U.S. Cl. ............ 15/105; 15/167.1; 15/22.1; 607/79; 604/20

(58) Field of Classification Search .................... 15/105, 15/167.1, 22.1; 601/21, 20, 79; 607/79; 604/20
See application file for complete search history.

(56) References Cited

U.S. PATENT DOCUMENTS

| 4,691,718 A | * | 9/1987 | Sakuma et al. ................. 433/32 |
| 2005/0283928 A1 | * | 12/2005 | Grez et al. ..................... 15/22.1 |

(Continued)

FOREIGN PATENT DOCUMENTS

| JP | 56-97034 | * | 8/1981 |
| JP | 59-143329 | * | 9/1984 |

(Continued)

OTHER PUBLICATIONS

International Search Report dated May 19, 2009, issued in PCT/JP2009/057597.

(Continued)

*Primary Examiner* — Mark Spisich
*Assistant Examiner* — Andrew A Horton
(74) *Attorney, Agent, or Firm* — Edwards Wildman Palmer LLP; James E. Armstrong, IV; George N. Chaclas

(57) ABSTRACT

The electronic toothbrush (10) includes a brush head (20) having an implantation area where bristles (22) for brushing of teeth are fixed and a handle (21) configured to carry the brush head (20). The brush head (20) includes a brush electrode exposed on its surface. The brush electrode includes a first electrode (23) located in the implantation area where the bristles (22) are fixed and a second electrode (242) located in a non-implantation area where no bristles (22) are fixed. The handle (30) includes a handle electrode (32) exposed on its surface. The handle (30) is configured to house a power source (35) for applying a voltage between the handle electrode (32) and each of the first electrode (23) and the second electrode (242). The bristles (22) are fixed directly to the first electrode (24).

4 Claims, 8 Drawing Sheets

U.S. PATENT DOCUMENTS

2008/0083074 A1* 4/2008 Taniguchi et al. ............. 15/22.1
2008/0183249 A1* 7/2008 Kitagawa et al. ............... 607/79
2008/0271271 A1* 11/2008 Chan .............................. 15/22.2

FOREIGN PATENT DOCUMENTS

| JP | S59-143329 U * | 9/1984 |
| JP | 2560162 B2 | 7/1994 |
| JP | 7-17133 | 3/1995 |
| JP | 08-117030 A | 5/1996 |
| JP | 08-322642 A | 12/1996 |
| JP | 2007-202863 A | 8/2007 |

OTHER PUBLICATIONS

Japanese Official Action issued on Sep. 4, 2012, in corresponding Japanese Application No. 2010-508230.

* cited by examiner

FIG. 7A
FIG. 7B
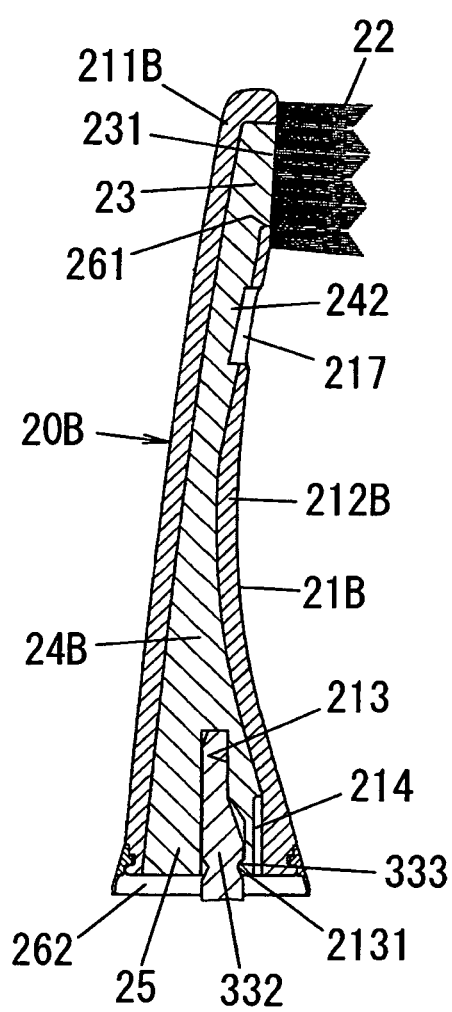
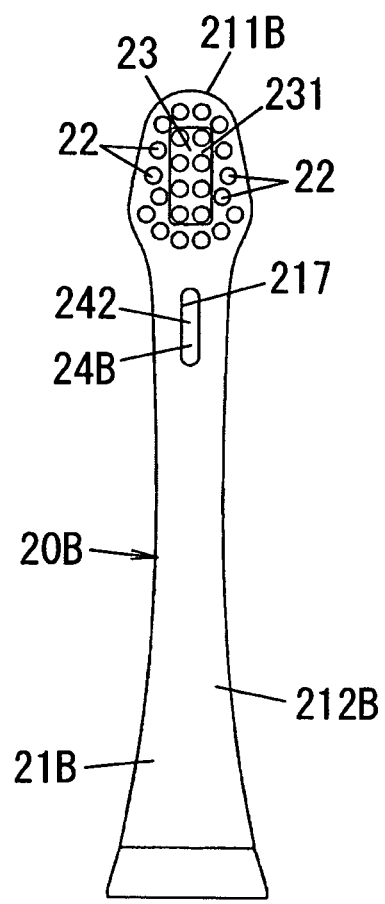

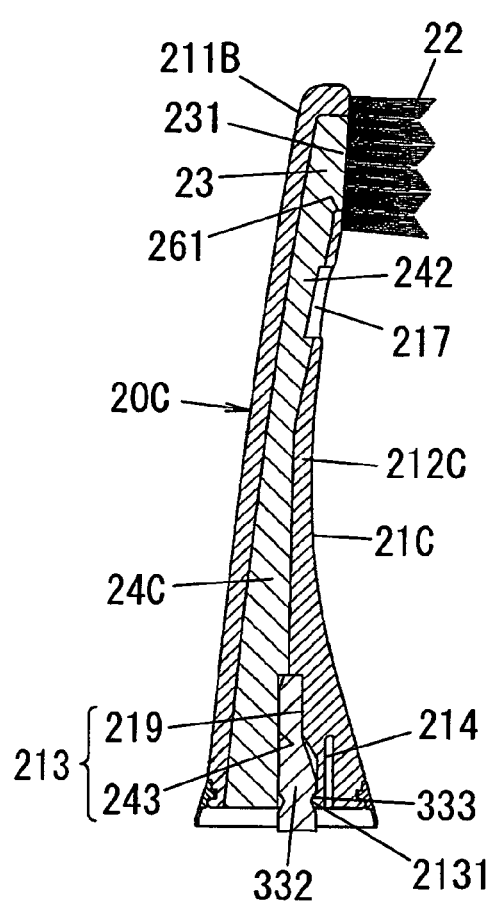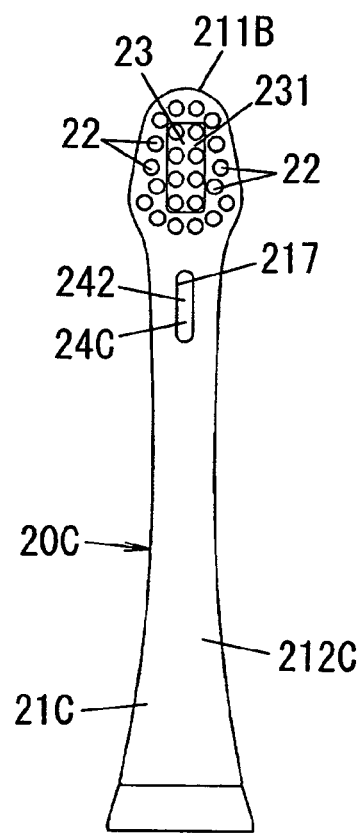

ELECTRONIC TOOTHBRUSH

CROSS-REFERENCE TO RELATED APPLICATION

This application is the U.S. national phase, pursuant to 35 U.S.C. §371, of International Application No. PCT/JP2009/0057597, published in Japanese on Oct. 22, 2009 as international publication No. WO 2009/128477 A1, which claims the benefit of Japanese Application Ser. No. 2008105988, filed Apr. 15, 2008, Japanese Application Ser. No. 2008105989, filed Apr. 15, 2008, and Japanese Application Ser. No. 2008105990, filed Apr. 15, 2008, the disclosure of which applications are incorporated herein in their entireties by this reference.

TECHNICAL FIELD

The present invention is directed to an electronic toothbrush configured to flow an electrical current into a user's oral cavity for promoting removal of dental plaque.

BACKGROUND ART

In the past, there has been proposed an oral hygiene device capable of preventing occurrence of alveolar pyorrhea and gingival inflammation by improving metabolism and a blood circulation of soft tissues surrounding the oral cavity. Thereby the oral hygiene device can improve oral hygiene.

For example, there has bee proposed an electronic toothbrush (ionic toothbrush) as a one type of the oral hygiene device (see Japanese Patent Publication No. 2560162). The electronic toothbrush weakens adherence developed between a tooth plane and dental plaque by flowing a weak current into the oral cavity (flowing an electrical current between the electronic toothbrush and teeth). Therefore, use of the electronic toothbrush is capable of removing the dental plaque.

The electronic toothbrush disclosed in the aforementioned Japanese patent publication includes a spindle connected to a negative pole of a power source and a terminal member connected to a positive pole in order to flow the weak current into the oral cavity. The terminal member is located on a handle. The spindle is exposed through an exposure groove in a neck. Liquid (e.g. saliva and solution of a dentifrice) in the oral cavity comes into contact with the spindle through the exposure groove during brushing of teeth. Thereby, electrical current flows between the spindle and the terminal member via user's body (the electrical current flows into the oral cavity).

However, in the above electronic toothbrush, the spindle is exposed through the exposure groove formed in the neck. Therefore, depending on an orientation of the electronic toothbrush during brushing of teeth, the liquid may be prevented from flowing into the exposure groove due to gravity acting on the brush. In this instance, the electronic toothbrush fails to flow the current into the oral cavity with a consequence of not achieving an effect of easily removing the dental plaque.

DISCLOSURE OF INVENTION

In view of the above insufficiency, the present invention has been aimed to provide an electronic toothbrush capable of flowing an electrical current into user's oral cavity successfully.

The electronic toothbrush in accordance with the present invention includes a brush head having an implantation area where bristles for brushing of teeth are fixed and a handle configured to carry the brush head. The brush head includes a brush electrode exposed on its surface. The brush electrode includes a first electrode located in the implantation area and a second electrode located in a non-implantation area where no bristles are fixed. The handle includes a handle electrode exposed on its surface. The handle is configured to house a power source for applying a voltage between the brush electrode and the handle electrode. The bristles are fixed directly to the first electrode.

According to this invention, the brush head includes a brush electrode composed of plural electrodes (the first electrode and the second electrode). Therefore, the liquid in the oral cavity can be easy to contact with the brush electrode irrespective of an orientation of the electronic toothbrush during brushing of teeth. Further, the bristles are directly fixed to the first electrode. Therefore, the bristles are kept contacting with the first electrode even when the bristles are deformed or tensed while a user brushes one's teeth. In addition, a capillary action caused by gaps between the bristles promotes the contact with the liquid in the oral cavity and the first electrode because the first electrode is exposed on the surface of the brush head. It is possible to flow an electrical current successfully into the oral cavity.

Preferably, the first electrode includes a protrusion extending from the surface of the brush head. The bristles are fixed directly to the protrusion.

In this case, an electrical current can easily flow into the oral cavity because the first electrode comes into contact with the liquid in the oral cavity at a greater area than in a case where no protrusion is provided. Further, the first electrode can receive less amount of dirt than in an instance where the first electrode is recessed inwardly of the brush surface.

Preferably, the power source includes a first pole to be electrically connected to the brush electrode and a second pole to be electrically connected to the handle electrode. The handle includes a projection for attaching the brush head to the handle. The projection has electrical conductivity and being electrically connected to the first pole of the power source housed in the handle. The brush head includes a conductor having electrical conductivity and is configured to electrically connect the projection to the brush electrode. The conductor is formed integrally with the brush electrode as well as a terminal connector provided with a recess shaped to receive the projection.

In this case, the number of parts for assembling the electronic toothbrush is decreased by comparison with an instance where the terminal connector, the brush electrode, and the conductor are provided as separate parts. Therefore, the production cost of the brush head can be lowered. Thus, a reliability of electrical connection of the projection and the brush electrode can be improved.

Preferably, the power source includes a first pole to be electrically connected to the brush electrode and a second pole to be electrically connected to the handle electrode. The handle includes a projection for attaching the brush head to the handle. The projection has electrical conductivity and is electrically connected to the first pole of the power source housed in the handle. The brush head includes a terminal connector provided with a recess shaped to receive the projection, a conductor configured to electrically connect the projection received in the recess to the brush electrode, and a brush body supporting the terminal portion and the conductor.

In this case, the terminal connector and the brush body are provided as separate parts. Accordingly, a complexity of a shape of the brush body does not deteriorate a dimension accuracy of the terminal connector (dimension accuracy of the recess). It is possible to improve the dimension accuracy of the recess.

BRIEF DESCRIPTION OF DRAWINGS

FIG. 7A is a cross sectional view illustrating a eighth modification of the brush head of the above electronic toothbrush, FIG. 7B is a front view illustrating the eighth modification of the brush head of the above electronic toothbrush, FIG. 8A is a cross sectional view illustrating a ninth modification of the brush head of the above electronic toothbrush, and FIG. 8B is a front view illustrating the ninth modification of the brush head of the above electronic toothbrush.

BEST MODE FOR CARRYING OUT THE INVENTION

Figure 1:
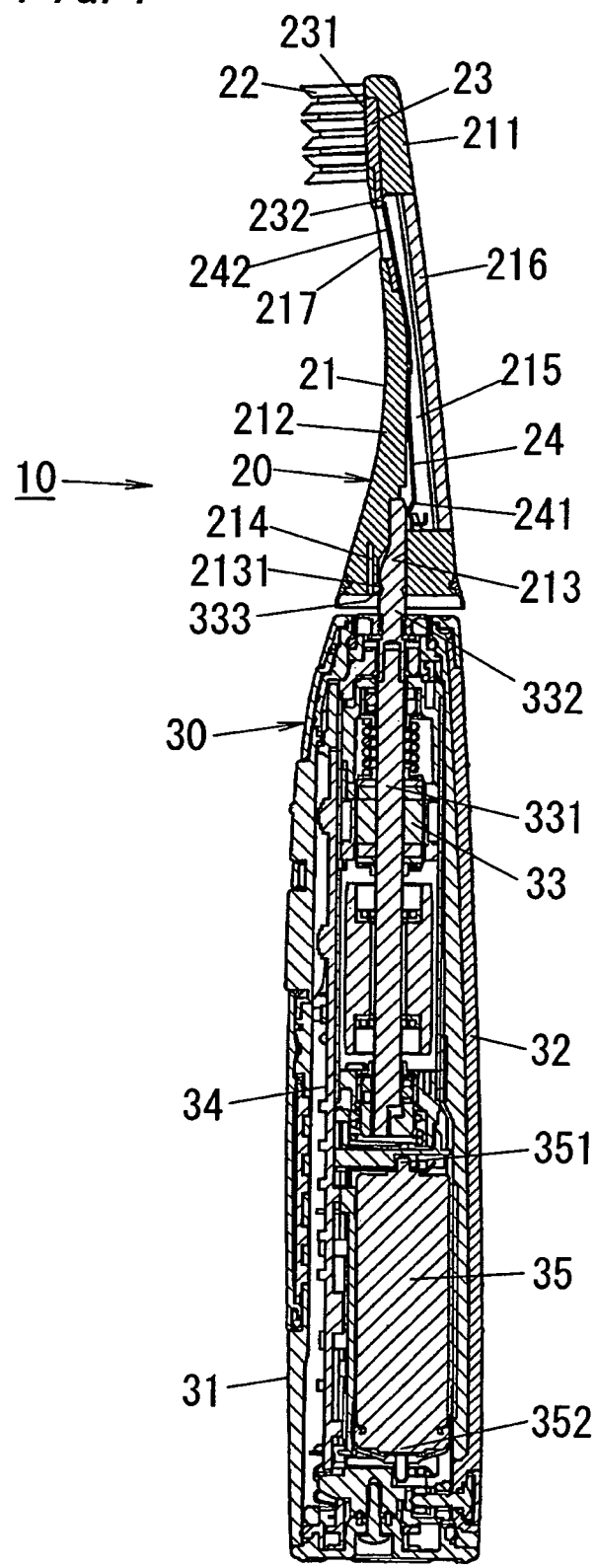
FIG. 1 is a cross sectional view illustrating an electronic toothbrush of an embodiment in accordance with the present invention.

As shown in FIG. 1, an electronic toothbrush 10 of an embodiment in accordance with the present invention includes a brush head 20 having an implantation area where bristles 22 for brushing of teeth fixed and a handle 30 configured to carry the brush head 20.

In the following explanation, for convenience, a leftward direction in FIG. 1 denotes a forward direction of the electronic toothbrush 10, and a rightward direction in FIG. 1 denotes a rearward direction of the electronic toothbrush 10. Vertical directions in each of FIGS. 1 and 2B denote a longitudinal direction of the electronic toothbrush 10, and a horizontal direction in FIG. 2B denotes a lateral direction of the electronic toothbrush 10.

The handle 30 includes an approximately cylindrical handle body 31. The handle body 31 is made of dielectric materials. The handle body 31 includes a handle electrode 32. The handle electrode 32 is exposed on a rear surface of the handle 30 to contact with a hand of a user who grasps the handle 30.

The handle 30 includes a drive device 33, a circuit board 34, and a power source 35. The handle body 31 houses the drive device 33, the circuit board 34, and the power source 35. Notably, the handle body 31 has a waterproof construction for preventing water from coming into an inside of the handle body 31.

The drive device 33 includes a shaft 331 to be linked to the brush head 20. The drive device 33 is configured to reciprocate the shaft 331 along the longitudinal direction. In other words, the drive device 33 is configured to reciprocate the brush head 20 along the longitudinal direction. There is a projection 332 attached to an apex of the shaft 331. The projection 332 extends from an apex of the handle body 31 to an outside of the handle body 31. The projection 332 and shaft 331 are made of electrically conductive materials. The projection 332 is provided in its front surface with a recess 333 for fixing the brush head 20. For example, a motor or an actuator employing a magnetic circuit can be adopted as the drive device 33.

The circuit board 34 includes a control circuit (not shown) configured to control the drive device 33. The control circuit includes a switch (not shown), for example. The control circuit is configured to provide an electrical power to the drive device 33 from the power source 35 in order to activate the drive device 33 when the switch is turned on. The control circuit is configured to provide no electrical power to the drive device 33 from the power source 35 while the switch is turned off. The circuit board 34 includes a boost circuit, a current limitation circuit, and the like, as necessary.

The electronic toothbrush 10 of the present embodiment is designed as an electric toothbrush having a configuration (the drive device 33 and the circuit board 34) for automatically reciprocating the brush head 20. However, the electronic toothbrush 10 need not include the configuration for automatically reciprocating the brush head 20. In short, the electronic toothbrush 10 may be designed as a manual toothbrush.

The power source 35 is a DC power source including a positive pole (second pole) 351 and a negative pole (first pole) 352. For example, the power source 35 can be selected from a primary cell (e.g. a dry cell) and a secondary cell (e.g. a lithium-ion cell, and a nickel-cadmium cell). In the case of the power source 35 being the secondary cell, preferably, the electronic toothbrush 10 is configured to allow the power source 35 to be charged by use of a contactless power transfer technique. In the case of the power source 35 being the primary cell, preferably, the electronic toothbrush 10 is configured to allow the power source 35 to be replaced easily.

In the handle 30, the shaft 331 and an electrical circuit (not shown) formed on the circuit board 34 electrically connect the projection 332 to the negative pole 351 of the power source 35. The circuit board 34 is provided with an electrical circuit (not shown) electrically connecting the handle electrode 32 to the positive pole 352 of the power source 35.

Figure 2A:
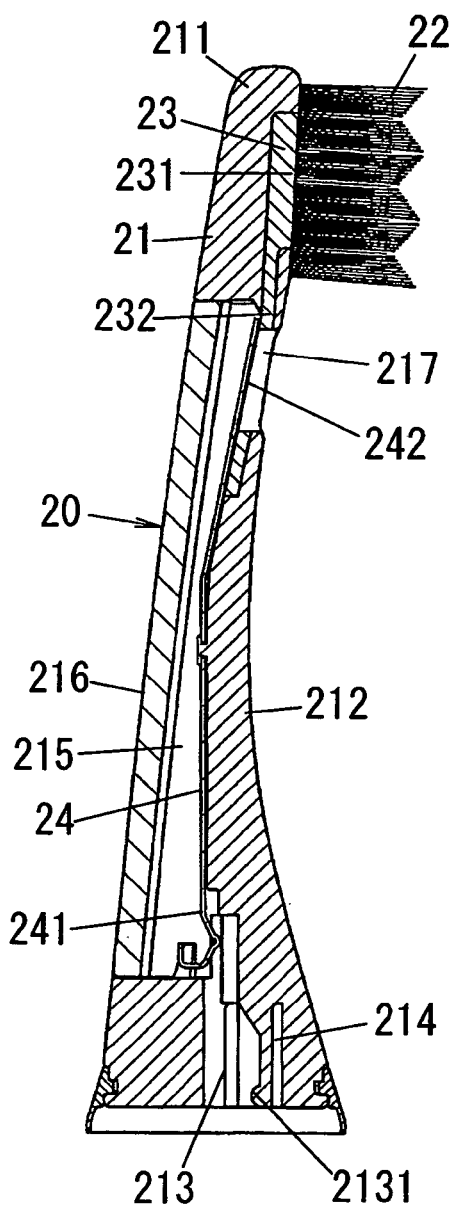
FIG. 2A is a cross sectional view illustrating a brush head of the above electronic toothbrush.
Figure 2B:
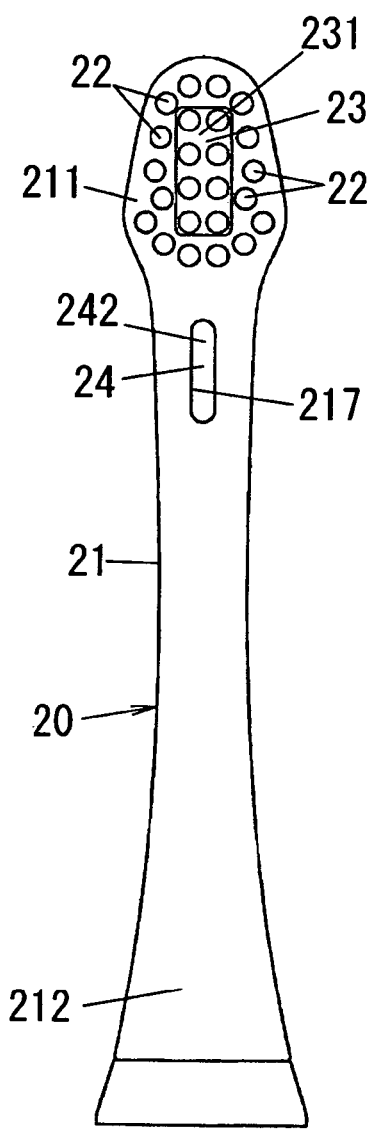
FIG. 2B is a front view illustrating the brush head of the above electronic toothbrush.

The brush head 20, as shown in FIGS. 2A and 2B, includes a brush body 21, the bristles (set of bristles) 22 for brushing of teeth, a first electrode 23, and a conductor 24.

The brush body 21 is made of dielectric materials. The brush body 21 includes a head 211 and a rod-like neck (shank) 212.

The head 211 is formed integrally at an upper end (first longitudinal end) of the neck 212.

The neck 212 is provided its lower end (second longitudinal end) with a recess 213 configured to receive the projection 332. A lock portion 2131, which is shaped to be fitted into a depressed portion 333 of the projection 332 received in the recess 213, is formed on an internal surface of the recess 213. The neck 212 is provided its rear surface with a clearance groove 214 such that the lock portion 2131 comes into resilient contact with the front surface of the projection 332. The brush head 20 is not easily detached from the handle 30 because the projection 332 is locked to the brush head 20 by engaging the lock portion 2131 in the depressed portion 333. A clicking engagement is made when the brush head 20 is attached to the handle 30.

The neck 212 includes a storage space 215 configured to store the conductor 24. The storage space 215 communicates to the recess 213 in the lower end side of the neck 212. The storage space 215 communicates to an outside of the neck 212 in the rear surface side of the neck 212. A cover 216 is attached to the rear side of the storage space 215 to conceal the storage space 215 therebehind. The cover 216 is made of dielectric materials. The cover 216 is attached to the neck 212 so as to prevent water from coming into the storage space 215.

There is an elongated opening 217, which expose the conductor 24, formed in the upper end (an end adjacent to the head 211) of the front surface of the neck 212.

The bristles 22 are fixed to a front surface of the head 211. For example, the bristles 22 are made of synthetic fibers. The synthetic fiber is a polyamide synthetic fiber such as a nylon, for example.

The first electrode 23 is embedded in the head 211. The first electrode 23, as shown FIG. 2B, includes an exposure portion 231 exposed on the front surface of the head 211 and a contacting portion 232 exposed to the storage space 215 of the neck 212.

The exposure portion 231 is located in the center portion of an area (hereinafter called "implantation area") of the head 211 where the bristles 22 are fixed. Therefore, the bristles 22 are directly fixed to the head 211 as well as the exposure portion 231. In the instance illustrated in FIG. 2, the exposure portion 231 has its outer periphery shaped into a rectangular shape. The exposure portion 231 has its front surface located in a coplanar relation with the front surface of the head 211.

The conductor 24 is made of electrically conductive materials and is shaped into an elongated plate shape. The conductor 23 is, as shown in FIG. 2A, stored in the storage space 215 of the neck 212. The conductor 23 has its first longitudinal end (upper end, in FIG. 2A) coming into contact with the contacting portion 232 of the first electrode 23. The conductor 23 is provided with a contacting terminal 241 exposed to the recess 213 at its second longitudinal end (lower end, in FIG. 2A). The contacting terminal 241 is designed to come into resilient contact with the projection 332 received in the recess 213. Therefore, it is possible to improve contact reliability of the conductor 24 and the projection 332. The conductor 24 includes a portion which is used as a second electrode 242 and exposed through the opening 217 of the neck 212.

As described in the above, the brush head 20 includes the first electrode 23 and the second electrode 242. Each of the first electrode 23 and the second electrode 242 is a brush electrode exposed on the surface of the brush head 20. The first electrode 23 is located in the implantation area where the bristles 22 are fixed. The second electrode 242 is located in a non-implementation are where no bristles 22 are fixed. The bristles 22 are directly fixed to the exposure portion 231 of the first electrode 23 being the brush electrode located in the implementation area.

As shown in FIG. 1, for attaching the brush head 20 to the handle 30, it is sufficient that the projection 332 of the handle 30 is engaged in the recess 213 of the brush head 20. Thereby, the brush head 20 is attached to the apex of the handle 30. The contacting terminal 241 of the conductor 24 is kept contacting with the projection 332 while the brush head 20 is attached to the handle 30.

Accordingly, the brush electrode (the first electrode 23 and the second electrode 242) is electrically connected to the negative pole 352 of the power source 35. By contrast, the handle electrode 32 is electrically connected to the positive pole of 351 the power source 35. That is, the power source 35 applies a voltage between the brush electrode and the handle electrode 32. As seen from the above, the brush electrode and the handle electrode 32 have polarities opposite to each other.

Since the electronic brush 10 includes the brush electrode composed of the first electrode 23 and the second electrode 242, the electronic brush 10 provides two electrical paths each flowing an electrical current into user's oral cavity. The first electrical path allows an electrical current to flow from the handle electrode 32 to the first electrode 23 via a user's body. The second electrical path allows an electrical current to flow from the handle electrode 32 to the second electrode 242 via the user's body.

The electronic toothbrush 10 includes the first electrode 23 exposed on the implementation area of the brush head 20. The first electrode 23 comes near to teeth or gums while the user brushes ones' own teeth. Therefore, because of that a liquid in the oral cavity easily contacts to the first electrode 23, an electrical current easily flows into the oral cavity. In particular, the bristles 22 are directly fixed to the first electrode 23. Therefore, the bristles 22 are kept contacting to the first electrode 23 even when the bristles 22 are deformed or tensed while the user brushes own teeth. Further, a capillary action caused by gaps between the bristles 22 promotes the contact of the liquid in the oral cavity and the first electrode 23.

While the user brushes one's own teeth with the bristles 22 directed upwardly, the liquid in the oral cavity is caused to flow from the head 211 to the neck 212 under an action of gravity. In this case, the liquid in the oral cavity may sometime fail to come into steady contact with the first electrode 23, causing no electrical current within the oral cavity.

However, the electronic toothbrush 10 is provided with the second electrode 242 in its neck 212. Therefore, the liquid of the oral cavity which has flowed from the head 211 to the neck 212 comes into contact with the second electrode 242. As seen in the above, even if the liquid of the oral cavity makes no contact with the first electrode 23, the liquid of the oral cavity comes into contact with the second electrode 242. In particular, the second electrode 242 is located in the opening 217 formed in the neck 212. The opening 217 can easily receive the liquid in the oral cavity. Therefore, the second electrode 242 can easily come into contact with the liquid in the oral cavity.

As described in the above, according to the electronic toothbrush 10, the liquid in the oral cavity comes into contact with either the first electrode 23 or the second electrode 242 irrespective of an orientation of the electronic toothbrush 10 while the user brushes own teeth.

According to the electronic toothbrush 10, since the brush electrode easily comes into contact with the liquid in the oral cavity, it is possible to flow an electrical current successfully into the oral cavity.

As a result, the electronic toothbrush 10 is capable of promoting removal of tooth plaque by weakening adherence developed between a tooth plane and the tooth plaque. Further, the electronic toothbrush 10 is capable of enhancing oral hygiene by improving metabolism and a blood circulation of soft tissues surrounding the oral cavity.

In the instance shown in FIGS. 1 and 2, the portion of the conductor 24 exposed through the opening 217 is used as the second electrode 242. However, the second electrode 242 may be provided as a separate part electrically coupled to the conductor 24. For example, the second electrode 242 is shaped into a shape fitted into the opening 217 or a shape covering the internal periphery of the opening 217.

The materials of each of the first electrode 23, the second electrode 242, and the handle electrode 32 are not limited to metals and can be selected from electrically-conductive resins and electrically-conductive rubbers. The important point is that each of the first electrode 23, the second electrode 242, and the handle electrode 32 has electrical conductivity.

FIGS. 3 to 8 illustrate modifications of the brush head 20, respectively.

Figure 3A:
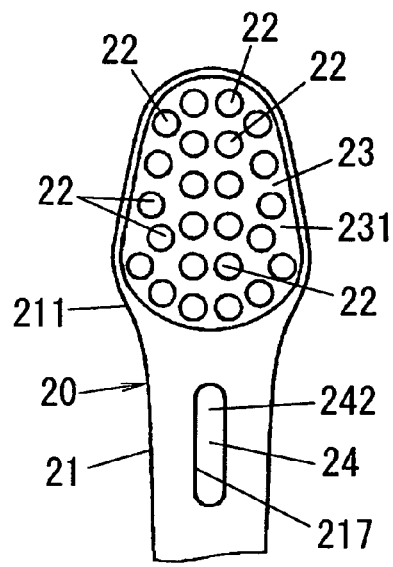
FIG. 3A is a partial front view illustrating a first modification of the brush head of the above electronic toothbrush.
Figure 3B:
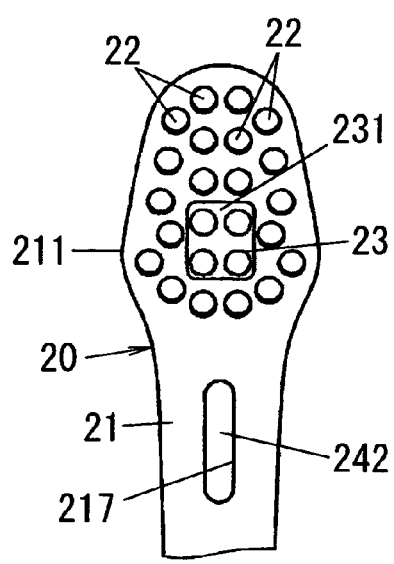
FIG. 3B is a partial front view illustrating a second modification of the brush head of the above electronic toothbrush.
Figure 3C:
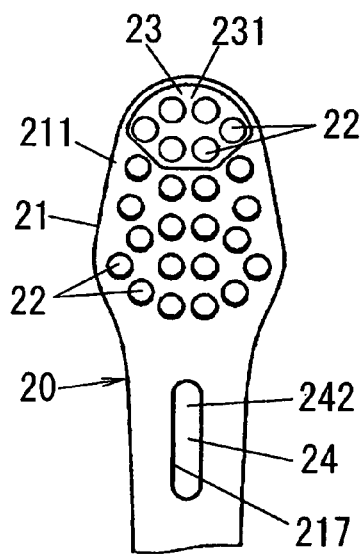
FIG. 3C is a partial front view illustrating a third modification of the brush head of the above electronic toothbrush.
Figure 3D:
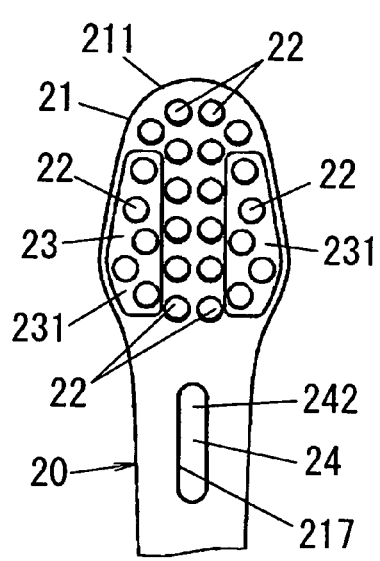
FIG. 3D is a partial front view illustrating a fourth modification of the brush head of the above electronic toothbrush.

The modification illustrated in FIG. 3A has the exposure portion 231 exposed on the entire implantation area. In other words, the entire front surface of the exposure portion 231 is used as the implantation area. In the modification illustrated in FIG. 3B, the exposure portion 231 has its peripheral shape shaped into a square shape (approximately square shape). The exposure portion 231 exposed on the front surface of the head 211 is smaller in an area than that illustrated in respective FIGS. 1 and 2. The modification illustrated in FIG. 3C has the exposure portion 231 exposed on the upper portion of the font surface of the head 211. The modification illustrated in FIG. 3D has the first electrode 23 includes the two exposure portions 231. The two exposure portions 231 are spaced from each other along the lateral direction of the electronic toothbrush 10. Briefly, the exposure portion 231 is only required to be exposed on the implantation area. The exposure portion 231 may be exposed on any area within the implantation area. The number of the exposure portions 231 is not limited to one and may be two or more.

Figure 4A:
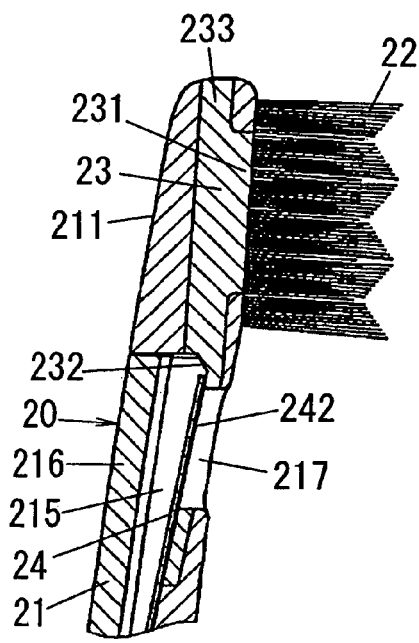
FIG. 4A is a cross sectional view illustrating a fifth modification of the brush head of the above electronic toothbrush.
Figure 4B:
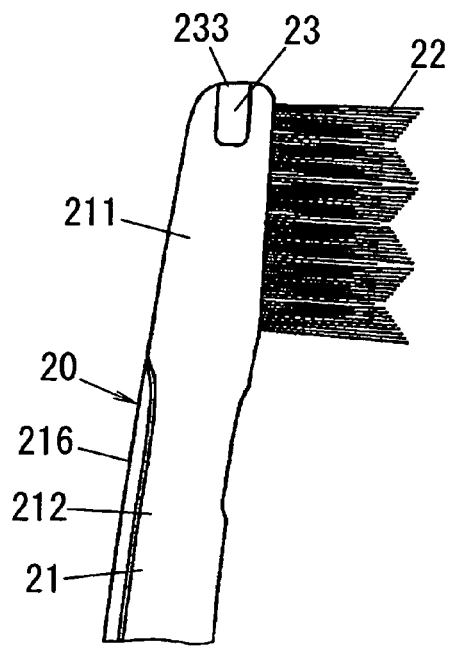
FIG. 4B is a side view illustrating the fifth modification of the brush head of the above electronic toothbrush.
Figure 4C:
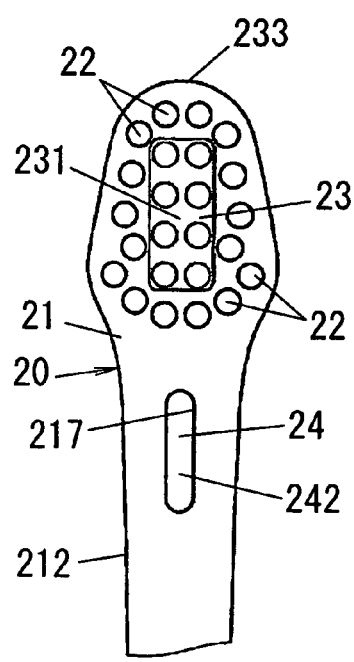
FIG. 4C is a front view illustrating the fifth modification of the brush head of the above electronic toothbrush.

In modifications shown in respective FIGS. 4A to 4C, the first electrode 23 includes an exposure portion (second exposure portion) 233 exposed on a side surface of the upper end (the first longitudinal end) of the head 211 in addition to the exposure portion (first exposure portion) 231.

Therefore, even if the user brushes own teeth with the bristles 22 directed downwardly, the liquid in the oral cavity comes into contact with the second exposure portion 233. Thus, it is possible to flow an electrical current successfully into the oral cavity.

The first electrode 23 may include, instead of or in addition to the second exposure portion 233, a third exposure portion (not shown) exposed on a rear surface of the head 211 and/or a fourth exposure portion exposed on a lateral side surface of the head 211. The liquid in the oral cavity easily comes into contact with the first electrode 23, as the number of the portions of the first electrode exposed on the surface of the head 211 is increased. Accordingly it is possible to flow an electrical current successfully into the oral cavity.

Figure 5:
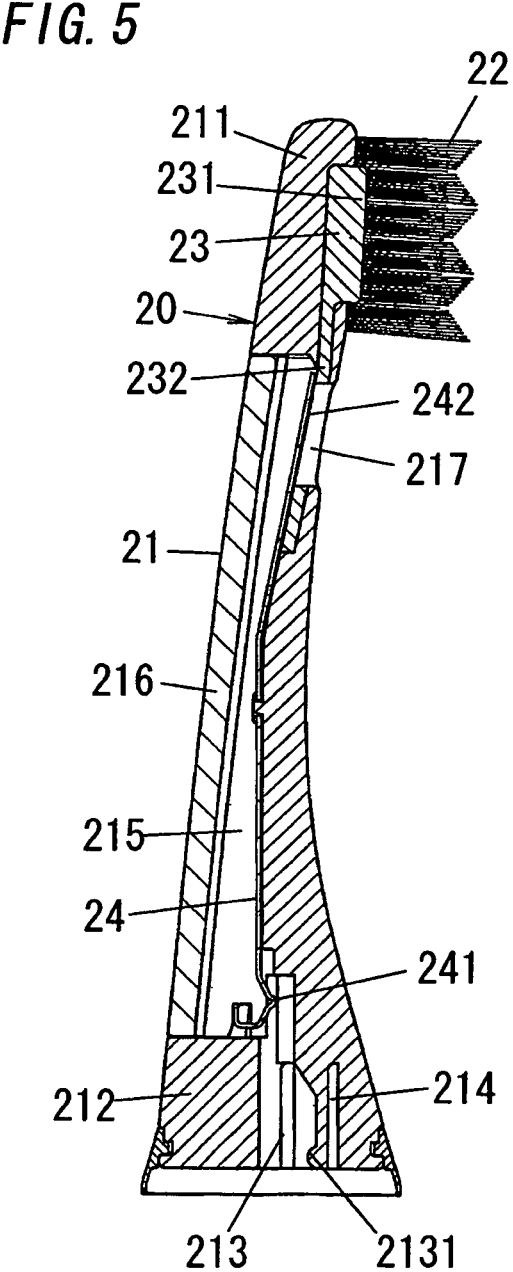
FIG. 5 is a cross sectional view illustrating a sixth modification of the brush head of the above electronic toothbrush.

The modification illustrated in FIG. 5 includes the exposure portion 231 having its front surface located anteriorly relative to the front surface of the head 211. In other words, the exposure portion 231 is a protrusion extending from the surface of the brush head 20.

According to the brush head 20 illustrated in FIG. 5, an area of the portion of the first electrode 23 where the liquid in the oral cavity comes into contact is increased by comparison with the instance shown in FIG. 2 where the first electrode 23 includes no protrusion (in short, the exposure portion 231 has its front surface located in a coplanar relation with the front surface of the head 211). Thus, the electrical current can easily flow into the oral cavity.

Further, according to the brush head 20 illustrated in FIG. 5, the first electrode 23 can receive less amount of dirt than in an instance where the first electrode 23 is recessed inwardly of the surface of the brush 20 (in short, the head 211 has its front surface located anteriorly relative to the front surface of the exposure portion 231).

As shown in FIG. 5, the first electrode 23 may be provided with the exposure portion 231 which has its entire front surface extending from the front surface of the head 211. Alternatively, the first electrode 23 may be provided with the exposure portion 231 which has a part of its front surface extending from the front surface of the head 211.

Figure 6:
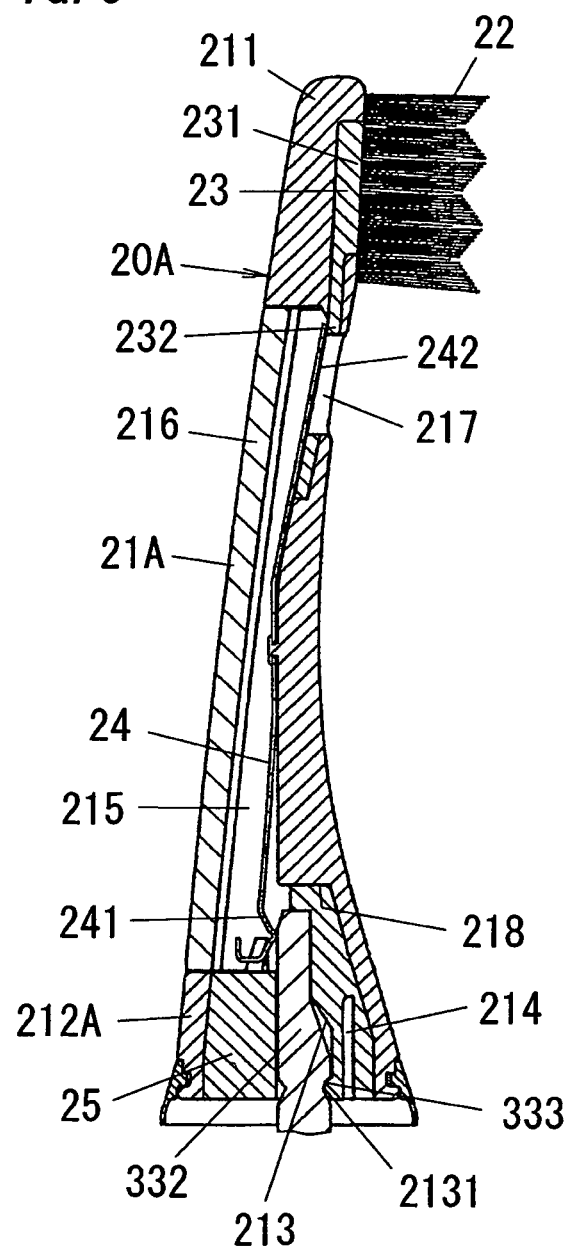
FIG. 6 is a cross sectional view illustrating a seventh modification of the brush head of the above electronic toothbrush.

In the modification illustrated in FIG. 6, the brush head 20A includes a terminal connector 25 in addition to the brush body 21A, the bristles 22, the first electrode 23, and the conductor 24.

The terminal connector 25 is made of dielectric resins. The terminal connector 25 includes the recess 213 and the clearance groove 214. The terminal connector 25 is, further, provided with the lock portion 2131 on its interior surface.

The brush head 21A includes the head 211 and the neck 212A. The neck 212A includes, instead of the recess 213, a reception recess 218 configured to receive the terminal connector 25. In the brush body 21A, the reception recess 218 and the storage space 215 communicates to each other. Further, while the terminal connector 25 is received in the reception recess 218, the recess 213 of the terminal connector 25 communicates to the storage space 215.

The terminal connector 25 and the conductor 24 are attached to the brush body 21A. Therefore, in the brush head 20A, the brush body 21 and a portion (terminal connector 25) provided with the recess 213 are provided as separate parts.

Accordingly, a dimension accuracy of the terminal connector 25 (dimension accuracy of the recess 213 and the lock portion 2131) does not suffer from a deterioration caused by a complexity of a shape of the brush body 20A.

As described in the above, the brush head 20A shown in FIG. 6 is capable of improving the dimension accuracy of the recess 213 and the lock portion 2131 even when an interior shape of the brush head 20A becomes complex for attaching the conductor 24 to the brush body 20A. As a result, it is possible to reduce product-to-produce variations in respect of a force required to attach the brush head 20 to the handle 30, and to detach the brush handle 20 from the handle 30, and also a clicking force of attaching the brush head 20 to the handle 30.

In the modification shown in FIGS. 7A and 7B, the brush head 20B includes the brush body 21B, the bristles 22, the first electrode 23, the conductor 24B, and the terminal connector 25.

The conductor 24B is made of electrically conductive materials. The conductor 24B is formed integrally with the first electrode at its upper end (first longitudinal end) and formed integrally with the terminal connector 25 at its lower end (second longitudinal end). In the instance shown in FIG. 7, the terminal connector 25 is made of electrically conductive metals.

The brush body 21B is made of electrically conductive resins and is shaped into a rod shape. The brush body 21B is configured to incorporate the conductor 24B which is formed integrally with the first electrode 23 as well as the terminal conductor 25. The brush body 21B includes the head 211B and the neck 212B.

The head 211B includes a first exposure aperture 261. The first exposure aperture 261 exposes the front surface of the exposure portion 231 of the first electrode 23.

The neck 212B includes a second exposure aperture 262 and the opening 217. The second exposure aperture 261 exposes a surface, where the recess 213 is formed, of the terminal conductor 25, that is, a bottom surface of the conductor 24B (lower surface, in FIG. 7A). The brush head 20B also includes the portion, which is used as the second electrode 242, of the conductor 24B exposed through the opening 217.

As described in the above, in the brush head 20B shown in FIG. 7, the conductor 24B is formed integrally with the brush electrode (the first electrode 23 and the second electrode 242) as well as the terminal connector 25 provided with the recess 213 shaped to receive the projection 332.

Therefore, it is possible to decrease the number of parts for assembling the electronic toothbrush 10 by comparison with the instance (the brush head 20A shown in FIG. 6) where the terminal connector 25, the brush electrode (first electrode 23 and the second electrode 242), and the conductor 24 are provided as separate parts. Therefore, it is possible to lower the production cost of the brush head 20B than that of the brush head 20A. In particular, the contact reliability of the conductor 24B and the projection 332 is improved because the terminal connector 25 has the electrical conductivity. Therefore, it is possible to improve a reliability of electrical connection of the projection 332 and the brush electrode.

Further, the terminal connector 25 and the brush body 21B are provided as separate parts. Therefore, the dimension accuracy of the terminal connector 25 (dimension accuracy of the recess 213 and the lock portion 2131) does not suffer from the deterioration caused by the complexity of the shape of the brush body 20B. Accordingly, like the brush head 20A, the brush head 20B is capable of improving the dimension accuracy of the recess 213 and the lock portion 2131.

In the modification illustrated in FIGS. 8A and 8B, the brush head 20C includes the brush body 21C, the bristles 22, the first electrode 23, and the conductor 24C.

The conductor 24C is made of electrically conductive materials. The conductor 24C is provided with the first electrode 23 at its upper end (first longitudinal end). The conductor 24C is provided with a first groove 243 in a lower end portion (second longitudinal end portion) of its front surface.

The brush body 21C is made of electrically conductive resins and is shaped into a rod shape. The brush body 21C is configured to incorporate the conductor 24C which is formed integrally with the first electrode 23. The brush body 21C includes the head 211B and the neck 212C.

The neck 212C includes a second groove 219 opposed to the first groove 243 of the conductor 24C. The neck 212C is provided with the lock portion 2131 in an internal surface of the second groove 219. The neck 212C further includes the clearance groove 214 and the opening 217. The brush head 20C also includes the portion, which is used as the second electrode 242, of the conductor 24B exposed through the opening 217.

Concerning the brush body 21C, a space constituted by the first groove 243 and the second groove 219 is corresponding to the recess 213. Therefore, the conductor 24C and the brush body 21C catch the projection 332 between the conductor 24C and the brush body 21C. At this time, the lock portion 2131 presses the projection 332 against the conductor 24C. Therefore, the contact reliability of the conductor 24C and the projection 332 is improved.

As described in the above, in the brush head 20C shown in FIG. 8, the conductor 24C is formed integral with the brush electrode (the first electrode 23 and the second electrode 242). In addition, the first groove 243 of the conductor 24C and the second groove 219 of the neck 212 constitute the recess 213 configured to receive the projection 332.

Therefore, it is possible to decrease the number of parts for assembling the electronic toothbrush 10 by comparison with the instance (the brush head 20A shown in FIG. 6) where the terminal connector 25, the brush electrode (first electrode 23 and the second electrode 242), and the conductor 24 are provided as separate parts. Therefore, the production cost of the brush head 20B can be lowered than that of the brush head 20A. Thus, the reliability of electrical connection of the projection 332 and the brush electrode can be improved.

The invention claimed is:

1. An electronic toothbrush comprising:
a brush head having an implantation area where bristles for brushing of teeth are fixed; and
a handle configured to carry said brush head,
wherein said brush head includes a brush electrode exposed on its surface,
said handle including a handle electrode exposed on its surface, and
said handle being configured to house a power source for applying a voltage between said brush electrode and said handle electrode, and
wherein said brush electrode includes a first electrode located in said implantation area and a second electrode located in a non-implantation area where no bristles are fixed,
said bristles being fixed to a front surface of said brush head,
said first electrode being embedded in said brush head,
said first electrode including:
a first exposure portion exposed on said front surface of said brush head; and
a second exposure portion exposed on a side surface or a rear surface of said brush head, and
said bristles being fixed directly to said first exposure portion of said first electrode.

2. An electronic toothbrush as set forth in claim 1, wherein said first electrode includes a protrusion extending from the surface of said brush head, and
said bristles being fixed directly to said protrusion.

3. An electronic toothbrush as set forth in claim 1, wherein said power source includes a first pole to be electrically connected to said brush electrode and a second pole to be electrically connected to said handle electrode, said handle including a projection for attaching said brush head to said handle, said projection having electrical conductivity and being electrically connected to said first pole of said power source housed in said handle, said brush head including a conductor having electrical conductivity and being configured to electrically connect said projection to said brush electrode, and said conductor being formed integrally with said brush electrode as well as a terminal connector provided with a recess shaped to receive said projection.

4. An electronic toothbrush as set forth in claim 1, wherein said power source includes a first pole to be electrically connected to said brush electrode and a second pole to be electrically connected to said handle electrode, said handle including a projection for attaching said brush head to said handle, said projection having electrical conductivity and being electrically connected to said first pole of said power source housed in said handle, and said brush head including a terminal connector provided with a recess shaped to receive said projection, a conductor configured to electrically connect said projection received in said recess to said brush electrode, and a brush body supporting said terminal portion and said conductor.

* * * * *

UNITED STATES PATENT AND TRADEMARK OFFICE
CERTIFICATE OF CORRECTION

PATENT NO.        : 8,413,285 B2
APPLICATION NO.   : 12/735583
DATED             : April 9, 2013
INVENTOR(S)       : Tomohiro Kunita et al.

It is certified that error appears in the above-identified patent and that said Letters Patent is hereby corrected as shown below:

Title page, item (73), delete "Panasonic Electric Works Co., Ltd., Osaka (JP)" and replace with "Panasonic Corporation, Kadoma-shi (JP)"

Signed and Sealed this
Fifteenth Day of October, 2013

Teresa Stanek Rea
*Deputy Director of the United States Patent and Trademark Office*